(12) United States Patent
Munoz et al.

(10) Patent No.: US 10,182,884 B2
(45) Date of Patent: Jan. 22, 2019

(54) SYSTEMS AND METHODS FOR MANUFACTURING ORTHODONTIC APPLIANCES

(71) Applicant: Ormco Corporation, Orange, CA (US)

(72) Inventors: Deric Marc Munoz, Ontario, CA (US); Philip Blair Corrin, Alta Loma, CA (US); Billy Chiman Yim, Chino, CA (US); Siu-Kau Tam, San Dimas, CA (US)

(73) Assignee: Ormco Corporation, Orange, CA (US)

( * ) Notice: Subject to any disclaimer, the term of this patent is extended or adjusted under 35 U.S.C. 154(b) by 1424 days.

(21) Appl. No.: 13/869,406

(22) Filed: Apr. 24, 2013

(65) Prior Publication Data

US 2013/0285268 A1    Oct. 31, 2013

Related U.S. Application Data

(60) Provisional application No. 61/638,617, filed on Apr. 26, 2012.

(51) Int. Cl.
*A61C 7/12*    (2006.01)
*B22F 3/00*    (2006.01)
(Continued)

(52) U.S. Cl.
CPC ............. *A61C 7/12* (2013.01); *A61C 7/14* (2013.01); *B01D 11/00* (2013.01); *B01D 15/00* (2013.01);
(Continued)

(58) Field of Classification Search
None
See application file for complete search history.

(56) References Cited

U.S. PATENT DOCUMENTS 4,731,208 A * 3/1988 Nakajima .......... B01D 11/0203
264/28
5,271,903 A  12/1993 Durst et al.
(Continued)

FOREIGN PATENT DOCUMENTS

CN    101006942 A    8/2007
CN    101068503 A    11/2007
(Continued)

OTHER PUBLICATIONS

Chartier, T; Bordet, F; Delhomme, E; Baumard, J; Extraction of Binder from Green Ceramic Bodies by Supercritical Fluid: Influence of the Porosity, 2002, Journal of the European Ceramic Society, 22, pp. 1403-1409.*
(Continued)

*Primary Examiner* — Jeffrey M Wollschlager
*Assistant Examiner* — Armand Melendez
(74) *Attorney, Agent, or Firm* — Wood Herron & Evans LLP

(57) ABSTRACT

A system for debinding a green body in the form of an orthodontic appliance may include a pressure vessel configured to contain a supercritical fluid. A source of a fluid chemical may be coupled to the pressure vessel to supply the fluid chemical to the pressure vessel. A heat source may be configured to heat the fluid chemical. A pump may pressurize the fluid chemical to at least the supercritical pressure. A collection vessel is coupled to the pressure vessel to capture the binder removed from the green bodies as at least the pressure of the supercritical fluid is reduced. A method of manufacturing an orthodontic appliance includes exposing green bodies including particles and a binder to a supercritical fluid to remove at least some of the binder from the green bodies, and collecting the removed binder from the super-
(Continued)

critical fluid as the supercritical fluid transitions to a non-supercritical fluid.

18 Claims, 2 Drawing Sheets

(51) Int. Cl.
*B01D 11/00* (2006.01)
*B01D 15/00* (2006.01)
*A61C 7/14* (2006.01)
*B22F 3/10* (2006.01)
*A61C 13/00* (2006.01)
*B22F 3/22* (2006.01)
*C22C 14/00* (2006.01)
*C22C 32/00* (2006.01)

(52) U.S. Cl.
CPC .............. *B22F 3/00* (2013.01); *B22F 3/1025* (2013.01); *A61C 13/0006* (2013.01); *B22F 3/22* (2013.01); *C22C 14/00* (2013.01); *C22C 32/0031* (2013.01)

(56) References Cited

U.S. PATENT DOCUMENTS

| 5,613,849 | A | 3/1997 | Tanaka et al. |
| 2009/0169841 | A1* | 7/2009 | Abels .................... B28B 11/12 428/206 |

FOREIGN PATENT DOCUMENTS

| DE | 3545913 | A1 | 7/1986 |
| EP | 0664998 | A1 | 8/1995 |
| EP | 2098495 | A2 | 9/2009 |
| JP | S61155265 | A | 7/1986 |
| JP | S6311577 | A | 1/1988 |
| JP | 5-43317 | | 2/1993 |
| JP | H06501936 | A | 3/1994 |
| JP | H07252111 | A | 10/1995 |

OTHER PUBLICATIONS

Abeln, B.; Effects of a Combined Supercritical Extraction/Thermal Cycle on Binder Removal, Cycle Time, Yield, Residual Carbon, and Effect Formation in Multilayer Ceramic Capacitors, Dec. 2010.*

Martina, R; Laino, A., Cacciafesta V.; Cantiello P.; Recycling Effects on Ceramic Brackets: a Dimensional Weight and Shear Bond Strength Analysis, 1997, European Journal of Orthodontics, 19, 629-636.*

Search Report issued in European Patent Apploication No. 13165404.8; dated Jul. 25, 2013; 11 pages; European Patent Office.

Sang Woo Kim; "Debinding behaviors of injection molded ceramic bodies with nano-sized pore channels during extraction using supercritical carbon dioxide and n-heptane solvent"; The Journal of Supercritical Fluids; 2010; pp. 339-344.

Fleur Bordet et al.; "The use of co-solvents in supercritical debinding of ceramics"; Journal of the European Ceramic Society; 2002; pp. 1067-1072.

Goceram AB, Supercritical CO2 Extractors [online], [retrieved on Jan. 31, 2012]; retrieved from the Internet: <URL: www.goceram.com/supercritical-extraction.htm>, 4 pp.

Chinese Patent Office, First Office Action issued in corresponding CN Application No. 201310218226.2 dated Sep. 23, 2016, 16 pages, including English translation.

The Journal of Supercritical Fluids, United States, 2010, vol. 51, No. 3, p. 339-344.

Journal of the European Ceramic Society, Britain, 2002, vol. 22, No. 7, p. 1067-1072.

Japanese Patent Office, Office Action issued in corresponding Japanese Patent Application No. 2013-93559 dated Mar. 27, 2017, 9 pages.

* cited by examiner

SYSTEMS AND METHODS FOR MANUFACTURING ORTHODONTIC APPLIANCES

CROSS-REFERENCE TO RELATED APPLICATION

This application claims priority to U.S. Provisional Patent Application Ser. No. 61/638,617, filed Apr. 26, 2012, the disclosure of which is incorporated by reference herein in its entirety.

TECHNICAL FIELD

The present invention relates generally to systems and methods for manufacturing orthodontic appliances.

BACKGROUND

Orthodontic treatment often involves attaching an appliance to the tooth. Forces applied to the appliance are then transferred to, and thus move, the tooth. As such, orthodontic appliances represent a principal component of corrective orthodontic treatment devoted to improving a patient's dentition. Orthodontic appliances may include brackets, archwires, or other devices.

Using the orthodontic bracket as an example, an orthodontist may affix orthodontic brackets to the patient's teeth with an adhesive and engage an archwire into a slot of each bracket. The archwire exerts flexural and/or torsional stresses on the orthodontic brackets to create restorative forces, including rotation, tipping, extrusion, intrusion, translation, and/or torque forces, tending to bring the teeth toward a desired position. Traditional ligatures, such as small elastomeric O-rings or fine metal wires, may be employed to retain the archwire within each bracket slot. Due to difficulties encountered in applying an individual ligature to each bracket, self-ligating orthodontic brackets have been developed that eliminate the need for ligatures by relying on a movable portion or member, such as a latch, clip, or slide, for retaining the archwire within the bracket slot.

Various materials have dominated the orthodontic market because of their characteristic combination of strength, toughness, aesthetics, biological/corrosion resistance, and manufacturability. For example, archwires used early in orthodontic treatment may be made of shape memory alloys (SMAs) with superelastic properties that have corrosion resistance. Nitinol is a well-known shape-memory alloy and is an alloy of nickel (Ni) and titanium (Ti). By way of additional example, archwires may be made of stainless steel or a Ti-containing alloy, such as, a titanium molybdenum alloy (TMA). Each of these metals combines some level of strength, toughness, and corrosion resistance. Similarly, orthodontic brackets are ordinarily formed from stainless steel, which is strong, nonabsorbent, weldable, and relatively easy to form and machine. Titanium and titanium alloy brackets are also available as nickel-free alternatives to stainless steels. Though titanium is more corrosion resistant than stainless steel, titanium is more expensive and more difficult to manufacture than stainless steel.

As an alternative to the metallic orthodontic brackets, certain orthodontic brackets incorporate a bracket body of a transparent or translucent non-metallic material, such as a ceramic, that assumes or mimics the color or shade of the underlying tooth. However, as compared to their metallic counterparts, ceramic orthodontic brackets have a comparatively low strength and toughness. Furthermore, ceramic appliances are difficult and costly to manufacture.

Injection molding processes are capable of producing intricately formed parts, such as, metallic or ceramic orthodontic appliances. The parts formed are often referred to as green bodies and include a formed mixture of unsintered powder and binder. The unsintered powder may include metallic or ceramic powder. Powder injection molding (PIM) with either of these powders may be referred to as metal injection molding (MIM) or ceramic injection molding (CIM), respectively. The mixture of unsintered powder and binder is heated to soften the binder and the heated mixture is then injected into a mold. Once injected, the binder cools and hardens so as to hold the particles together in the injection molded form. To form the final product, the binder is removed. The binder-free bodies are then heated to an elevated temperature to sinter the particles together, thus consolidating the powder particles into a sintered body. Subsequent finishing operations may be required to transform the sintered body into the final orthodontic appliance.

To form the orthodontic appliances via MIM or CIM processes, the binder material must be removed during subsequent processing. This process may be referred to as debinding. Typically, the green bodies are therefore subject to a process whereby the binder is removed. Removal of the binder is often achieved by heating the green body in a furnace to an elevated temperature at which the binder decomposes or gasifies. A flow of gases inside the furnace transports the gasified or decomposed binder away from the green body. In addition to furnaces or thermal-based systems, chemical-based and water-based systems are also known methods for removing the binder from the green body. Depending on the size of the green body and the type of binder, as well as other factors, removal of the binder may take a significant period of time, typically in the range of hours, if not longer. Thus, long periods required for binder removal delay subsequent sintering operations and result in an overall lengthening of the manufacturing process. Furthermore, each of these processes may utilize significant amounts of energy, require expensive and/or bulky equipment, and produce a waste stream of gases or other chemicals that are typically the subject of environmental regulation.

Consequently, there is a need for improved systems and methods of manufacturing orthodontic appliances that overcome these and other deficiencies.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

DETAILED DESCRIPTION

Figure 2:
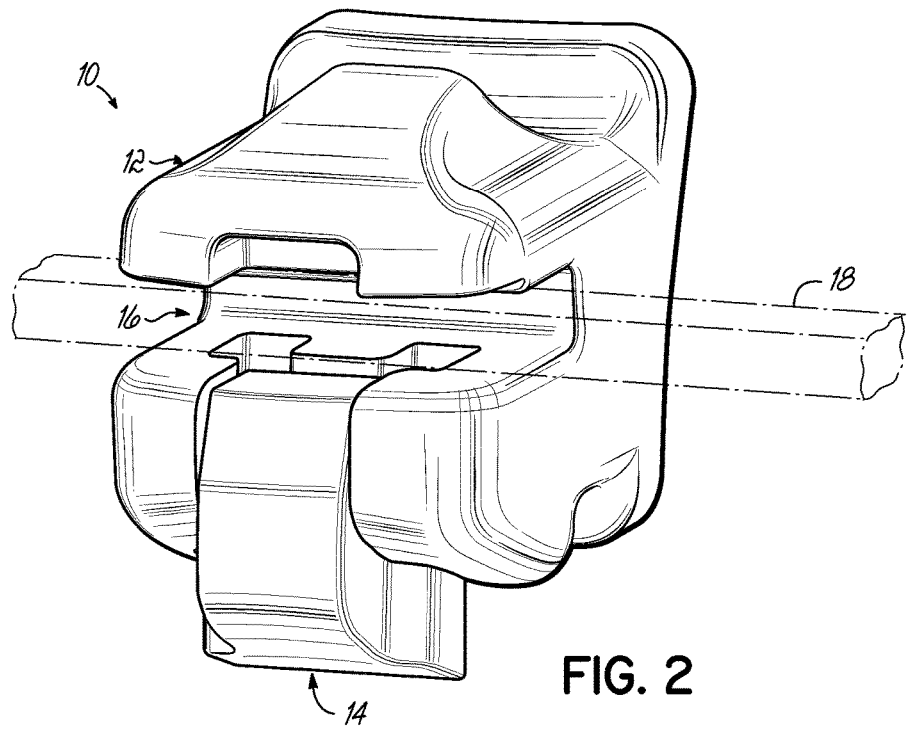
FIG. 2 is a perspective view of a self-ligating orthodontic bracket made according to one embodiment of the method of the present invention with a ligating latch shown in the opened position.
Figure 3:
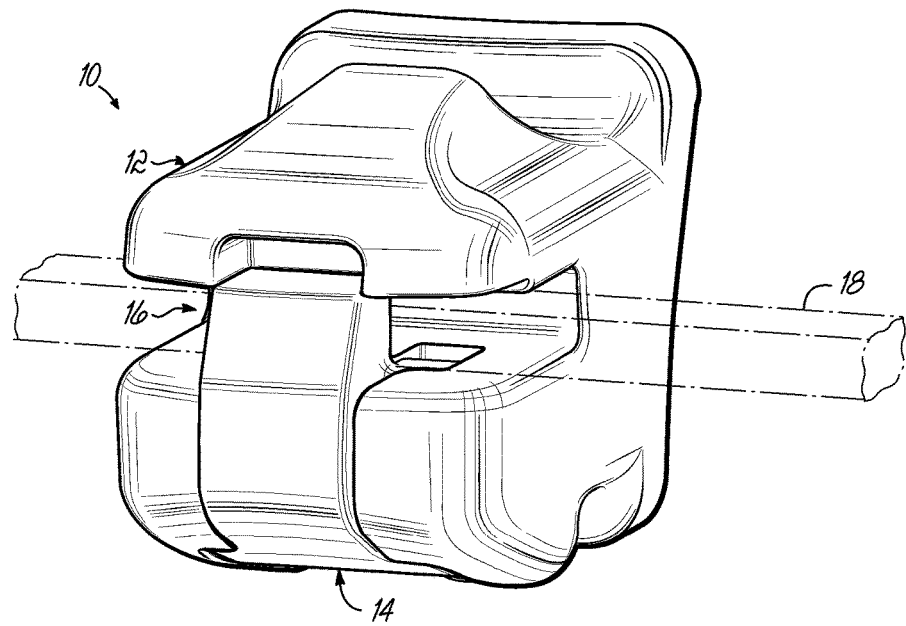
FIG. 3 is a perspective view of the self-ligating orthodontic bracket shown in FIG. 2 with the ligating latch shown in a closed position.

To address the shortcomings of existing processes and systems, a system according to embodiments of the present invention utilizes a supercritical fluid to debind a green body in the form of an orthodontic appliance. The system is thus configured to expose the green body, including a mixture of metallic particles or ceramic particles and a binder, to the supercritical fluid. The supercritical fluid may remove all or a portion of the binder while leaving behind the particles of the green body. Following binder removal, the particles, which retain their green-body shape, may be sintered and subject to additional processes by which an orthodontic appliance may be manufactured. As used herein, an orthodontic appliance refers to components used in orthodontic treatment. By way of example, orthodontic appliances include, but are not limited to, orthodontic brackets, as is illustrated in FIGS. 2 and 3; archwires; other appliances that may be attached or secured directly or indirectly to a tooth; or tools used in orthodontic treatment. The system may remove the binder more quickly than thermal-based debinding systems, such as, furnaces, while also reducing the energy necessary to remove the same volume of binder. In one embodiment, the volume of binder removed per hour is substantially higher than a thermal debinding system. In addition, according to embodiments disclosed herein, the system reduces the volume of binder that is released into the environment because the system captures or collects at least a portion of, if not all of, the binder removed from the green body.

Figure 1:
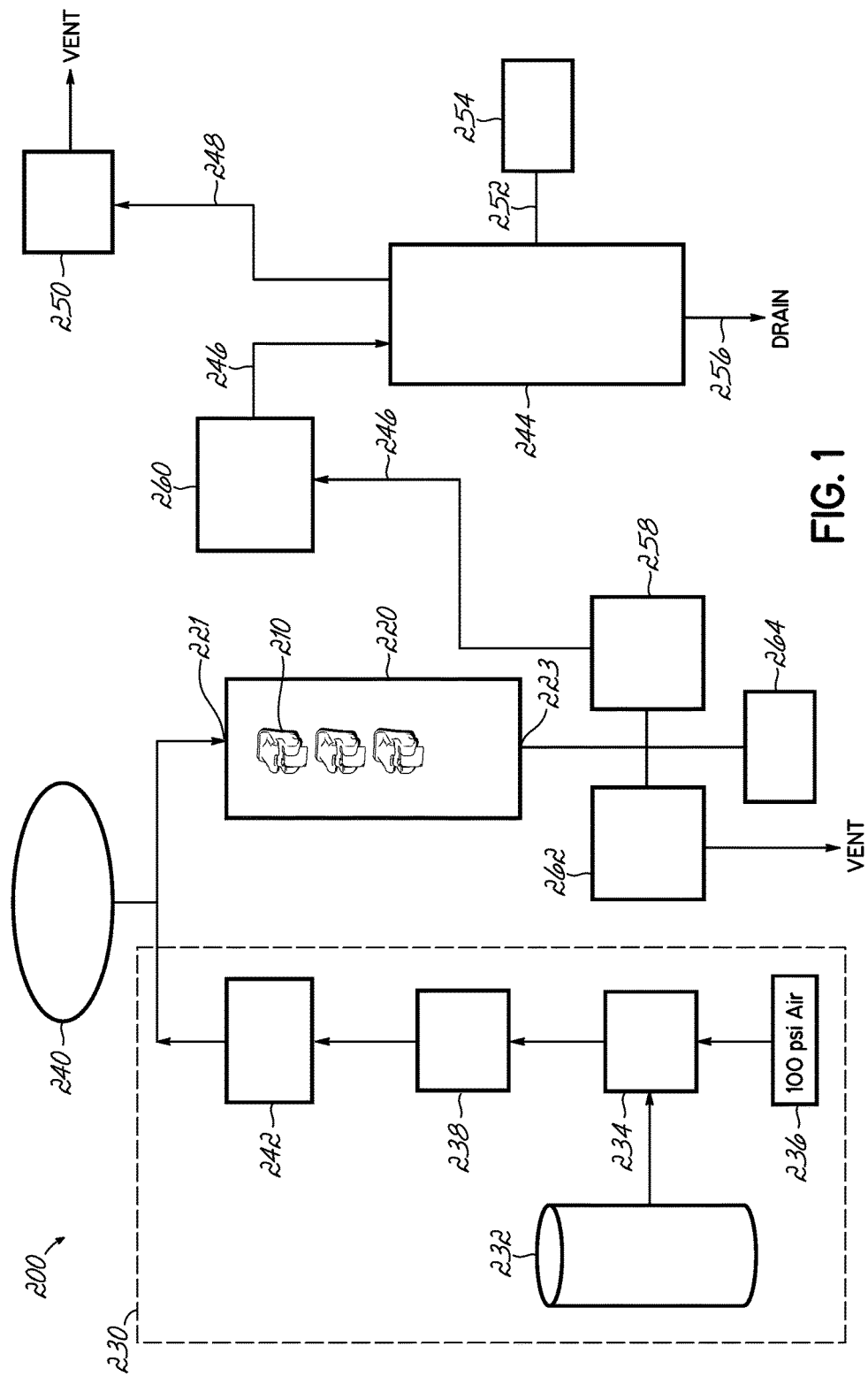
FIG. 1 depicts a schematic representation of a debinding system according to one embodiment of the invention.

To these and other ends, FIG. 1 illustrates a system 200 for debinding a plurality of green bodies 210. As set forth briefly above, a green body is a three-dimensional body that includes sinterable particles held together by a binder. The green bodies 210 may be made by an injection molding process, such as, by a metal injection molding (MIM) process or by a ceramic injection molding (CIM) process, as are known in the art. By way of example and not limitation, the green body 210 may resemble an orthodontic appliance, such as an orthodontic bracket, though larger in volume while in the green, unsintered state. The density of the green body may be decreased following debinding due to removal of the binder and the volume and density may decrease following sintering due to a reduction in the porosity of the body. The sinterable particles may include ferrous metallic particles, for example, stainless steels, such as 17-4 stainless steel and 3-16 stainless steel, and non-ferrous metallic particles, for example, titanium or titanium alloy, or other metallic alloy particles or mixtures thereof. The sinterable particles may alternatively include ceramic particles, for example, particles of alumina ($Al_2O_3$) or particles of another metal oxide. The metallic or ceramic particles in the green body are of sufficient average size and distribution so as to sinter at an elevated temperature corresponding to the particular material.

In addition to sinterable particles, the green body 210 includes a binder. As set forth above, the binder holds the sinterable particles together during formation of the green body 210 and is later removed during debinding of the green body and before sintering. The binder may include an organic binder, such as, a wax, which may include hydrocarbons and esters of fatty acids. For example, the binder may include paraffin wax, polystyrene, polyethylene, polypropylene, and/or stearic acid. It will be appreciated, however, that other organic binders are contemplated which may be sufficient to hold the sinterable particles together in the form of the green body 210. These include various polymers, such as, polyolefins, acrylics, latexes, polypropylene, polyethylene, polystyrene, and polyvinyl alcohol, to name only a few. The green body 210 may optionally contain other materials, such as, additives to facilitate molding of the green body and/or materials that aid the sintering process.

The proportion of sinterable particles in the green body 210 may depend on the orthodontic appliance being manufactured and/or the material of the sinterable particles and the binder. By way of example, the proportion of sinterable particles may range from about 25 wt. % to about 98 wt. %, though the proportion of sinterable particles may range from about 50 wt. % to about 98 wt. % and by way of further example may range from about 90 wt. % to about 95 wt. % of the green body 210. In one embodiment, the green body 210 weighs less than about $\frac{1}{10}$ of a gram, for example, about 0.06 g with the binder content being less than about $\frac{1}{100}$ of a gram, for example, about 0.005 g. The relative ratio of the weight of sinterable particles to the weight of binder may depend on the type of binder and the type of particles in the green body 210. In one embodiment, the proportional balance of the green body 210 is the binder. That is, in this case, the green body 210 consists essentially of the sinterable particles and the binder. As used herein, "consisting essentially of" means that no other materials are intentionally added to the green body 210. However, molding aids, sintering aids, and impurity content of the raw materials or the fabrication process may be contemplated.

As shown in FIG. 1, the system 200 includes a pressure vessel 220. After forming, the green bodies 210 are placed into the pressure vessel 220 for debinding. While not shown, the green bodies 210 may be placed into crucibles or another fixture which is then placed into the pressure vessel 220. The pressure vessel 220 is configured to contain a chemical, described below, in a supercritical state. During the process of debinding bodies 210, as set forth herein, the pressure within the pressure vessel 220 may be elevated, for example, to about 5,000 psi, or to another pressure that exceeds the critical pressure required to form a supercritical fluid.

In addition to pressure, though not shown in FIG. 1, a heater may be positioned proximate the vessel 220 and be configured to heat the contents of the vessel 220 to elevated temperatures while at the elevated pressure. The elevated temperature within the vessel 220 may be sufficient to exceed the critical temperature required to form a supercritical fluid from the chemical, for example, the temperature of the pressure vessel 220 may be elevated to about 65° C. It will be appreciated, however, that the combination of the temperature and pressure within the pressure vessel 220 may be less than about 5,000 psi and/or less than about 65° C., though a supercritical fluid may form. Accordingly, during debinding, the green bodies 210 may be exposed to the supercritical fluid.

The pressure vessel 220 may be of sufficient size to contain a plurality of green bodies 210. By way of example, the pressure vessel 220 may enclose a volume of about 1 L and may be capable of containing or holding about 10,000 to about 15,000 green bodies, for example, about 12,000 green bodies, configured in the form of orthodontic brackets. However, the pressure vessel 220 may enclose a volume that is larger or smaller than 1 L. In this regard, in one embodiment, the ratio of the volume of the plurality of green bodies 210 to the usable chamber volume of the pressure vessel 220 is from about 10% to about 15% and by way of further example about 12.5%. It will be appreciated that the exposed surface area of green bodies is large. By way of example, the exposed surface area may be at least about 800 sq. in. and may range from about 850 sq. in. to about 2,000 sq. in. and by way of further example may range from about 900 sq. in.

to about 1,600 sq. in. The increase in exposed surface area per green body may facilitate or increase the binder removal rate.

The supercritical fluid may be formed from a fluid chemical which may exist initially in a gaseous state or initially in a liquid state. In one embodiment, in which the supercritical fluid is formed from a fluid chemical that initially exists as a liquid, a liquid supply system 230 is coupled to the pressure vessel 220 at an outlet 221 and is configured to supply a liquid chemical to the pressure vessel 220. To that end, the liquid supply system 230 may include a liquid source 232, which may include prefilled bottles of the liquid chemical and/or may include a continuous supply of the liquid chemical. By way of example and not limitation, the fluid chemical may include carbon dioxide ($CO_2$) so that the liquid source 232 may supply liquid $CO_2$ to the pressure vessel 220. It is contemplated, however, that the supercritical fluid may be formed from a fluid chemical that initially exists in the gaseous state so that embodiments of the present invention are not limited to forming a supercritical fluid from a liquid chemical, such as liquid $CO_2$. The liquid supply system 230 may supply the liquid at a flow rate of about 30 to about 40 liters per minute (lpm). However, higher and lower flow rates are contemplated, and the flow rate may depend on the size of the pressure vessel 220, the amount of liquid in the liquid source 232, and the temperature of the liquid therein.

In one embodiment, the liquid supply system 230 may include a pump 234 coupled to the liquid source 232. The pump 234 may be piston driven and require a source of compressed air 236 to pump the liquid chemical from the liquid source 232. For example, the compressed air 236 may provide an air pressure of about 100 psi or more to the pump 234. However, other pump configurations may be used to pump the fluid chemical from the source 232. The pump 234 may draw the liquid chemical through a siphon tube (not shown) positioned within the liquid source 232 or otherwise force the liquid chemical from the liquid source 232 into the pressure vessel 220. The pump 234 may also increase the pressure of the liquid chemical to a pressure above that of standard temperature and pressure (STP) (i.e., 14.504 psi) or a pressure at or above a pressure that exceeds a critical pressure of the liquid chemical to cause the liquid chemical to enter a supercritical phase.

With continued reference to FIG. 1, the liquid supply system 230 may further include a heater 238 for heating the liquid chemical supplied by the liquid source 232. To facilitate supercritical fluid formation, a heater 238 may heat the liquid chemical to a temperature that exceeds STP temperature, i.e., 0° C., or to a temperature at or above a critical temperature of the liquid chemical. In this regard, the combination of heat provided by the heater 238 and pressure provided by the pump 234 may cause the liquid chemical to become a supercritical fluid in the pressure vessel 220 and/or in the liquid supply system 230 just prior to entry into the pressure vessel 220. It will be appreciated that the heater 238 and the pump 234 may operate sequentially or simultaneously to heat and pressurize the liquid chemical.

In the supercritical phase, the liquid chemical is at or above its critical temperature and at or above its critical pressure. A supercritical phase is a fluid-like state in which the fluid chemical, which may initially be a gas or a liquid, adopts properties between a gaseous state and a liquid state. The fluid chemical may, for example, exist as a gas or liquid at STP, but embodiments of the invention are not limited thereto. As is known, a phase diagram of a substance may depict multiple phases at various combinations of temperature and pressure. For instance, these phases may include a gas phase, a solid phase, a liquid phase, and may also depict a supercritical fluid phase. By adjusting the temperature and the pressure of the substance, for example, a substance which is a gas at STP, the substance may be transformed into a solid, a liquid, or a supercritical fluid. This transformation is reversible. By way of example, where the gas is $CO_2$, the critical temperature is 31.1° C. and the critical pressure is about 1,071 psi. Thus, increasing the temperature and the pressure of $CO_2$ gas from STP to a temperature at or above a temperature of 31.1° C. and a pressure at or above a pressure of 1,071 psi will result in the formation of supercritical $CO_2$.

With reference to FIG. 1, in one embodiment, a pressure transducer 240 is used to measure the pressure of the liquid chemical at or near the pressure vessel 220. The pressure measurement may be utilized by a computer (not shown) to operate the pump 234 in a manner by which the pressure of the liquid chemical may be increased or decreased according to a predetermined process.

In one embodiment, once the liquid chemical is injected or flowed into the pressure vessel 220, the pressure vessel 220 containing green bodies 210 is sealed. The pressure and temperature inside the pressure vessel 220 may be adjusted so as to exceed the critical temperature and critical pressure required to cause a supercritical fluid to form.

As such and according to embodiments of the present invention, the green bodies 210 are exposed to the supercritical fluid. The pressure vessel 220 may be sealed so as to expose the green bodies 210 to the supercritical fluid for a fixed, predetermined period of time. That is, no flow from or into the pressure vessel 220 occurs during this "static" period. The supercritical fluid may thus dissolve or otherwise remove all or a portion of the binder from the green bodies 210. While it is possible to evacuate the pressure vessel 220 prior to filing it with the liquid chemical, the residual atmospheric gases in the pressure vessel 220 introduced on loading the green bodies 210 may not pose a problem for supercritical fluid formation.

After this initial "static" period, the supercritical fluid is released from the pressure vessel 220. It will be appreciated that the supercritical fluid, at the time that it is released from the pressure vessel 220, may be saturated or at least contain dissolved or removed binder from the green bodies 210. By way of example, the static period may last from about 1 minute to about 5 minutes or more. In one embodiment, all of the binder in the green bodies 210 is removed before the supercritical fluid is released from the pressure vessel 220.

In one embodiment, following release of the supercritical fluid and removed binder, additional, fresh liquid chemical is flowed toward the pressure vessel 220. That is, the fresh liquid chemical has yet to be exposed to binder and therefore does not contain dissolved binder. The pressure and temperature of the additional fresh liquid chemical may be adjusted, as set forth above, by the pump 234, the heater 238, and/or the pressure vessel heater (not shown) to cause the additional fresh liquid chemical to enter the supercritical phase in or near the pressure vessel 220. This may be referred to as a "dynamic stage" of the debinding process.

During the dynamic stage, the flow of liquid chemical or fresh supercritical fluid into and out of the pressure vessel 220 may be continuous and may remove or dissolve any remaining or residual binder in the green bodies 210. The dynamic stage may last for about 30 minutes to about 60 minutes. With one or both of the static and/or dynamic flow of the supercritical fluid through the vessel 220, the binder removal rate may range from about 0.5 g per minute to about 1 g per minute. The debinding process may therefore take about 31 minutes to about 90 minutes depending on the configuration and number of green bodies 210 positioned in the pressure vessel 220. This may be compared to a thermal debinding process of the same number and type of green bodies 210 that may take on the order of 24 hours.

With continued reference to FIG. 1, the system 200 may include additional components to facilitate debinding of the green bodies 210. For example, an inlet valve 242 may separate the pressure vessel 220 from the liquid source 232. The valve 242 may be automatically opened and closed, such as by a PLC or other computer, to allow liquid chemical to flow into the vessel 220 at a predetermined time, temperature, and/or pressure.

In one embodiment, the system 200 further includes a collection vessel 244 coupled to the pressure vessel 220. As the supercritical fluid is released from the pressure vessel 220, it flows toward the collection vessel 244 through a pipe or tubing 246. Once the supercritical fluid leaves the pressure vessel 220, the pressure and the temperature of the supercritical fluid may begin to drop. As such, the solubility of the binder in the supercritical fluid may also drop and result in separation of the binder from the supercritical fluid in the tubing 246 prior to reaching the collection vessel 244.

In one embodiment, to maintain a predetermined temperature in the tubing 246 between the collection vessel 244 and the pressure vessel 220, insulation (not shown) may encircle the tubing 246 and heaters may be positioned to provide heat to the tubing 246. The tubing 246 may extend only a limited distance over which the temperature may be more uniformly controlled. By way of example, the tubing 246 may be less than 2½ feet long, and by way of further example, may be between about 1 foot and about 2 feet long. In one embodiment, the tubing 246 is about 1½ feet long. In addition, the diameter the tubing may be larger than about ⅛ inch in diameter, for example, the tubing 246 and have an internal diameter of about ¼ inch. As the supercritical fluid enters a non-supercritical state or becomes a non-supercritical fluid, for example, the supercritical fluid transitions back to a liquid phase or other fluid phase, any binder that begins to separate from the gas in the tubing 246 may remain heated so that it flows into the collection vessel 244. By way of example, the heater may heat the contents of the tubing 246 to a temperature of about 100° C. or more, for example, to a temperature of about 180° C. It will be appreciated that the configuration of the tubing 246 and heaters with insulation may reduce or eliminate the probability that the separated binder clogs the tubing 246 at the above-identified removal rates. In addition, in one embodiment, a pressure regulator 260 is positioned in the tubing 246 to control the pressure drop of the supercritical fluid therein.

Furthermore, at some point between the pressure vessel 220 and the collection vessel 244 or at the collection vessel 244, the supercritical fluid may wholly or partially transform back to the liquid phase as one or both of the temperature and pressure continues to fall below the necessary critical values. When this occurs, the binder may separate from the resulting liquid or other phase and is captured in the collection vessel 244 for later removal. In this regard, the pressure of the fluid in the collection vessel 244 may be controlled in a manner to allow it to drop below the critical pressure. However, the temperature within the collection vessel 244 may be maintained at or above the temperature sufficient to keep the binder in a flowable state. By way of example, a heater (not shown) proximate collection vessel 244 may maintain the temperature within the collection vessel 244 at a temperature of about 90° C. or more.

In one embodiment, the system 200 includes a vent line 248 that extends from the collection vessel 244 and that vents fluid from the collection vessel 244 to the atmosphere. The vent line 248 may include a flowmeter 250 for measuring the rate of escape of the gas from the collection vessel 244. In one embodiment, the system 200 includes a relief line 252 and relief valve 254 coupled to the collection vessel 244 as a safety precaution to prevent over pressurization of the vessel 244.

In one embodiment, a drain line 256 is coupled to and extends from the collection vessel 244. As the binder is collected in the collection vessel 244 during each cycle of the static and/or dynamic stages, it may be drained from the collection vessel 244 and reclaimed via the drain line 256. Once the binder is removed from one set of green bodies, the binder-free bodies are removed from the pressure vessel 220 and subsequently sintered, and a new set of green bodies 210 may then be place within the pressure vessel 220.

The system 200 may further include an outlet valve 258 positioned between the pressure vessel 220 and the collection vessel 244. As with the inlet valve 242, the outlet valve 258 may be automatically controlled by the PLC or another computerized system (not shown) to open and close according to a predetermined schedule. By way of example, in the process described above, after the static stage, the outlet valve 258 may be opened to allow the supercritical fluid to escape from the pressure vessel 220 and flow toward the collection vessel 244. The outlet valve 258 may then be partially or fully open during any subsequent dynamic stage to further debind, if necessary, the green bodies 210.

The system 200 may further include an auto vent valve 262 coupled to the pressure vessel 220 at or near the outlet 223 of the pressure vessel 220. The auto vent valve 262 may be utilized to vent the pressure vessel 220 to atmospheric pressure and to bypass the collection vessel 244 and the outlet valve 258. By way of example, the auto vent valve 262 may be utilized near the end of the debinding process at which time the pressure vessel 220 must be allowed to equilibrate with atmospheric pressure for unloading and reloading of the green bodies 210.

The system 200 may further include a rupture disc 264 directly coupled to the outlet 223 of the pressure vessel 220. The rupture disc 264 may allow the pressure vessel 220 to vent to atmosphere in the event that the pressure vessel 220 becomes over-pressurized and each of the vent valve 262 and outlet valve 258 fail to open.

Referring now to FIGS. 2 and 3, there is shown an exemplary orthodontic bracket 10 that may be manufactured according to a process or with embodiments of the system 200 as set forth herein. The orthodontic bracket 10 is disclosed in U.S. patent application Ser. No. 12/540,638 filed on Aug. 13, 2008, which is incorporated by reference herein in its entirety.

As shown, the orthodontic bracket 10 includes a bracket body 12 and a movable closure member coupled to the bracket body 12. In one embodiment, the movable closure member may include a ligating slide 14 slidably coupled with the bracket body 12. In one embodiment, green bodies configured in the form of the bracket body 12 and the ligating slide 14 are made by a CIM process, as is set forth herein. The green bodies are then placed in system 200 and subject to a supercritical fluid debinding process described above. Following debinding, the green bodies are sintered so as to form the bracket body 12 and the ligating slide 14. It will be appreciated that a green body in the configuration of orthodontic bracket 10 may alternatively be made by a MIM process and debound according to embodiments disclosed herein. Furthermore, it will be appreciated that other green bodies in the configuration of other orthodontic appliances may be made by other PIM processes, debound, and sintered as described above.

As is shown, the bracket body 12 includes an archwire slot 16 formed therein adapted to receive an archwire 18 (shown in phantom) for applying corrective forces to the teeth. The ligating slide 14 is movable between an opened position (FIG. 2) in which the archwire 18 is insertable into the archwire slot 16, and a closed position (FIG. 3) in which the archwire 18 is retained within the archwire slot 16. The bracket body 12 and ligating slide 14 collectively form a self-ligating orthodontic bracket 10 for use in corrective orthodontic treatments.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A method of manufacturing an orthodontic appliance, comprising:
   exposing a plurality of green bodies including sinterable particles and a binder to a supercritical fluid in a pressure vessel to remove at least some of the binder from the green bodies;
   collecting the removed binder from the supercritical fluid in a collection vessel separate from the pressure vessel as the supercritical fluid transitions to a non-supercritical fluid,
   flowing the removed binder from the pressure vessel to the collection vessel via a tube that couples the pressure vessel to the collection vessel, and
   heating the removed binder as the binder flows through the tube.

2. The method of claim 1 wherein before exposing the green bodies, the method further comprises:
   injection molding the green bodies.

3. The method of claim 1 wherein prior to and/or during exposing the green bodies, the method further comprises:
   heating a fluid chemical that exists as a fluid at standard temperature and standard pressure to a temperature equal to or greater than a critical temperature of the fluid chemical, and
   pressurizing the fluid chemical to a pressure equal to or greater than a critical pressure of the fluid chemical to form the supercritical fluid.

4. The method of claim 1 wherein exposing the green bodies includes exposing the green bodies to the supercritical fluid in a pressure vessel for a period of time during which there is no flow of the supercritical fluid from the pressure vessel or into the pressure vessel.

5. The method of claim 4 wherein, following exposing the green bodies to the supercritical fluid during the period of time during which there is no flow, exposing the green bodies includes flowing additional supercritical fluid into the pressure vessel and flowing the supercritical fluid out of the pressure vessel.

6. The method of claim 1 wherein collecting the removed binder includes cooling a temperature of the supercritical fluid below a critical temperature and/or reducing a pressure of the supercritical fluid below a critical pressure to form the non-supercritical fluid.

7. The method of claim 1 wherein, following exposing the green bodies to the supercritical fluid, the method further comprises:
   sintering the green bodies so as to consolidate the sinterable particles into sintered bodies.

8. The method of claim 7 wherein, following sintering, the method further comprises:
   finishing the sintered bodies so as to form orthodontic appliances.

9. The method of claim 1 wherein the supercritical fluid includes $CO_2$.

10. The method of claim 1 wherein the green bodies are in the configuration of orthodontic brackets.

11. The method of claim 1 wherein the green bodies weigh less than 1/10 of a gram each.

12. The method of claim 1 wherein the green bodies have a total exposed surface area of at least about 800 sq. in.

13. The method of claim 1 wherein the green bodies have a total exposed surface area in the range of from about 850 sq. in. to about 2,000 sq. in.

14. The method of claim 1 wherein the sinterable particles include metal particles or ceramic particles.

15. The method of claim 1 wherein, during flowing between the pressure vessel and the collection vessel, the pressure and/or the temperature of the supercritical fluid drops so that the supercritical fluid at least partially transforms to the non-supercritical fluid and the removed binder separates from the non-supercritical fluid.

16. The method of claim 15 wherein heating the removed binder includes maintaining the separated binder at a predetermined temperature at which the separated binder is flowable.

17. The method of claim 16 wherein the predetermined temperature at which the separated binder is flowable is less than a critical temperature of the supercritical fluid.

18. The method of claim 1 wherein collecting the removed binder from the supercritical fluid in the collection vessel includes venting the non-supercritical fluid in the collection vessel to the atmosphere.

* * * * *